United States Patent [19]

Coplans

[11] Patent Number: 4,681,113
[45] Date of Patent: Jul. 21, 1987

[54] CORSET

[75] Inventor: Carl W. Coplans, Cape Town, South Africa

[73] Assignee: Seton Products Limited, Oldham, England

[21] Appl. No.: 771,648

[22] Filed: Sep. 3, 1985

[30] Foreign Application Priority Data

Sep. 3, 1984 [ZA] South Africa ............... 84/6881

[51] Int. Cl.$^4$ .................... A41D 27/12; A41C 1/00
[52] U.S. Cl. ........................................ 450/134; 2/46
[58] Field of Search ............... 128/558, 78, 68, 96, 128/579 B, 573; 2/46

[56] References Cited

U.S. PATENT DOCUMENTS

| | | | |
|---|---|---|---|
| 2,304,699 | 12/1942 | Levy | 2/268 |
| 3,071,138 | 1/1963 | Eisen | 128/78 |
| 3,598,114 | 8/1971 | Lewis | 128/78 |
| 4,022,197 | 5/1977 | Castiglia | 128/78 |

FOREIGN PATENT DOCUMENTS

| | | |
|---|---|---|
| 236510 | 9/1925 | United Kingdom . |
| 274996 | 8/1927 | United Kingdom . |
| 985591 | 3/1965 | United Kingdom . |
| 1242826 | 8/1971 | United Kingdom . |
| 1245070 | 9/1971 | United Kingdom . |
| 1432945 | 4/1976 | United Kingdom . |
| 1501186 | 2/1978 | United Kingdom . |
| 1520722 | 8/1978 | United Kingdom . |
| 2086712 | 5/1982 | United Kingdom . |

Primary Examiner—Doris L. Troutman
Attorney, Agent, or Firm—Fisher, Christen & Sabol

[57] ABSTRACT

A corset comprises an inner waist encircling structure in the form of a band-like strip of elastic material releasably securable about a wearer's waist, and an outer waist encircling structure of flexible, inextensible material of variable length and an inflatable bag supported by at least one of said structures between the two structures means being provided for inflating the bag to apply inward pressure to the wearer's abdomen wall.

17 Claims, 2 Drawing Figures

CORSET

This invention relates to a corset for wear in the region normally occupied by a lumbo-sacral corset, hereinafter referred to as the waist area of a person, for example for therapeutic purposes in the treatment of spinal and/or posture conditions.

It is desirable for such purposes to provide a corset which can be adjusted to apply an inward force over an area of the wearer's abdominal wall to increase pressure on the abdomen and contents. If such pressure is applied by tightening an encircling girdle structure, the pressure is applied all around the wearer's body, and this can cause discomfort. The wholesale major adjustment which such tightening (or related slacking) may entail is difficult, particularly for older or disabled persons. It has accordingly been proposed to include one or more inflatable bags in a corset and to inflate the bag(s) after fitment of the corset. Examples of known corsets or corset-like structures including inflatable bags are shown in British Pat. Nos. 2086712, 1,520,722, 1,501,186, 1,432,945, 1,245,070, 1,242,826, 985,591, 274,996 and 236,510. Such inflation increases the corsets' effect without use of fastenings, but the accompanying changes in the shape of the corset body can cause localised discomfort and pinching of the wearer. It is an object of the present invention to provide a corset which is simple to adjust in its operating "intensity" and in which its load is uniformly distributed and which is comfortable to wear.

Accordingly, the invention provides a corset including a first, inner, band-like structure made from resiliently extensible material and adapted to encircle waists of different girths, and a second, outer, band-like structure of inelastic flexible material capable of securement around a wearer's waist overlying the first band and adaptable to waists of different girths, one of said structures mounting an inflatable bag disposed, in use, in a position overlying the wearer's abdomen. The bag may be inflated in situ, in which case means will be provided for inflating and deflating the bag.

According to a preferred feature of the invention the bag is disposed between the first and second band-like structures.

A preferred embodiment of corset of the invention may be characterised by one or more of the following features:

(a) there are two or more bags separately or individually inflatable;
(b) the first band-like structure is an elongate sheet of elastic textile material;
(c) the first band-like structure is adjustable in length by having overlappable end portions provided with complementary areas of hook/pile fasteners;
(d) the first band-like structure is adjustable in length by having its ends securable to each other by straps or connectors;
(e) the second band-like structure is an elongate sheet of inelastic textile material;
(f) the second band-like structure is in the form of an abdomen panel laterally connected to one or more straps securable about a wearer's waist;
(g) the second band-like structure comprises two spaced-apart straps, each attached to the first band-like structure at the back of the corset and each adjustably engaging the abdomen panel;
(h) the first and second band-like structures are secured to each other, permanently or releasably at the back of the corset;
(i) the first band-like structure includes one or more stiffeners extending transversely of its length;
(j) the abdomen panel is composed of a sheath which encloses the inflatable bag;
(k) the sheath has a rigid or semi-rigid plate on the outer side of the inflatable bag;
(l) the inflatable bag has a connected air-flor tube with a non-return valve, a pump bulb being provided for introducing air;
(m) the valve is compressible to cause it to distort and release air from the bag.

The invention will now be described further by way of example with reference to the accompanying drawings wherein.

Figure 1:
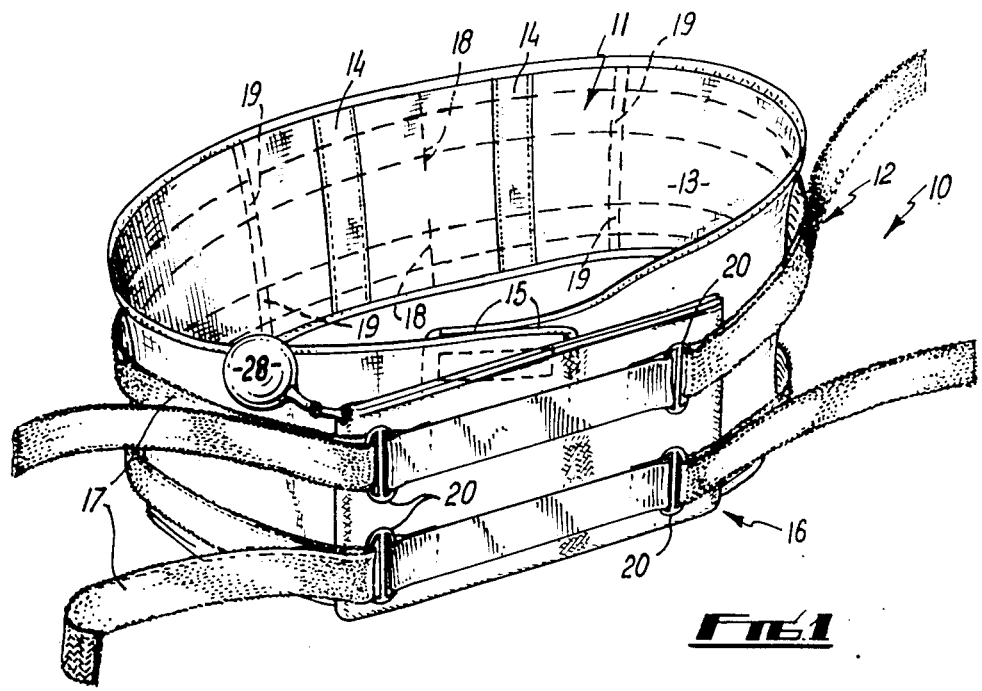
FIG. 1 is a perspective front view of a preferred corset of the invention.
Figure 2:
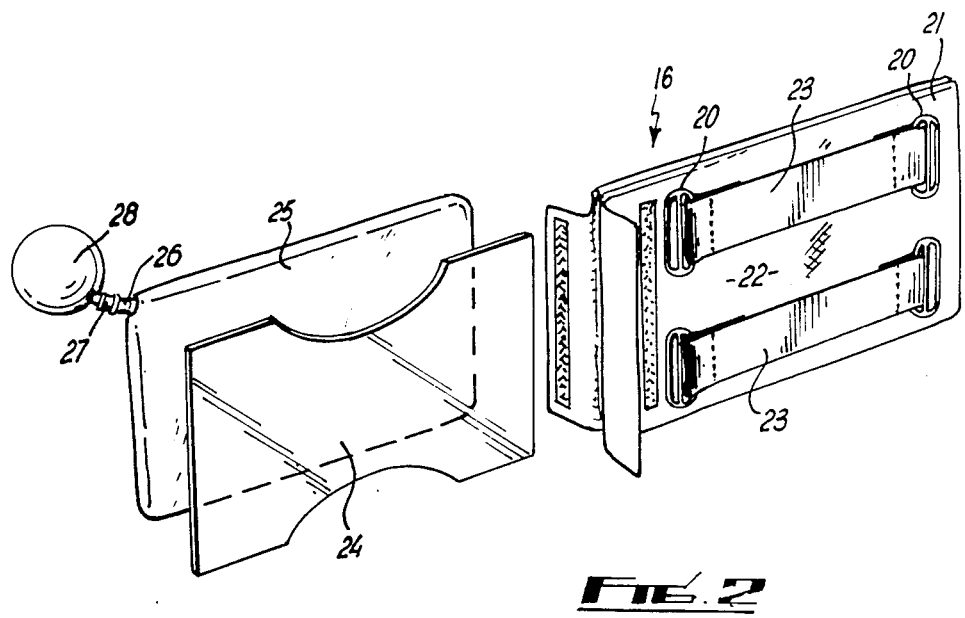
FIG. 2 is an enlarged perspective view showing an abdomen panel of the corset.

A preferred corset 10 of the invention comprises a first, inner, band-like structure 11, and a second outer band-like structure 12. Structure 11 is constituted by an elongate strip 13 of elastic or elasticated textile sheet material in one or more layers and presenting a smooth internal surface for contacting a wearer's skin. At the rear the strip 13 can have one or more flexible paravertebral stiffeners 14 accommodated in tunnels or pockets (not shown). The stiffeners serve to prevent rolling of the strip 13. Free end portions of the strip 13 have complementary overlapping strips of hook and pile material 15 enabling the corset to fit wearers of different girths.

Outer band-like structure 12 is constituted by an abdomen panel assembly 16 and a pair of spaced straps 17. Assembly 16 and straps 17 are inextensible, the straps being of textile material. Straps 17 are secured at their rear mid points 18 to the rear mid point of the strip 13 by one or more lines of stitching indicated in dotted lines. Outwardly spaced tape loops 19 support the straps 17 in juxtaposition with strips 13. Each free end portion of each strap 17 passes through a loop buckle 20 on the panel assembly 16 and is doubled back on and secured to itself. Respective parts of the facing sides of the straps 17 are provided with hook and pile material such as Velcro (Registered Trade Mark).

The abdomen panel assembly 16 comprises a rectangular sheath 21 to a front surface 22 of which a pair of tape strips 23 are sewn, ends of strips 23 mounting buckle loops 20. Sheath 21 accommodates a stiffening sheet 24 of plastics material against its outermost wall, which sheet is rigid or semi-rigid, and an inflatable bag 25 inwardly thereof. The bag 25 has an air-flow tube 26 with a valve 27 and inflation bulb pump 28. Valve 27 is normally non-return and maintains the bag 25 inflated. However, squeezing of valve 27 causes it to distort and leak to release air from bag 25.

In donning the corset 10, the wearer first wraps strip 13 around the waist, tensions it slightly by pulling the ends of strip 13 and presses the outer free end of strip 13 down on top of the inner free end to engage the hook and pile fastener strips 15 and securely locate the inner structure 11. The straps 17 are then tensioned relative to panel assembly 16 to cause the whole structure 12 closely and tightly to envelope and overlie the strip 13, but without exerting any considerable compressive force on the wearer. Inflation of the bag 25 say to an internal pressure of between 30 and 40 mm Hg, compresses the muscular wall of the abdomen, thus increasing the pressure on the contents of the abdomen, the load being evenly spread due to the unyielding nature of the sheet 24 and to the evening effect of the underlying strip 13. The increased pressure on the contents of the abdomen will increase the hydraulic-like thrust on the anterior surface of the lumbar spine, causing it to flex or straighten the lumbar curve. Furthermore, the hydraulic-like thrust lifts the wearer's diaphragm and diminishes axial stress on the lumbar spine.

The corset of the invention allows a considerable force to be uniformly applied to a wearer's abdmonial wall with great comfort and with minimal forward projection of the corset beyond the wearer, the degree of inflation of the bag 25 being chosen to apply a desired force to the abdomen wall according to the needs of the wearer, and the underlying strip isolating the wearer's skin from any creep or pinching forces due to lateral movement of parts of the sheath 21 surrounding the bag 25.

It will be appreciated that the nature of the structure herein proposed is such that a given corset may be used by persons of different girths, and that the number of sizes required to cater for the full range of girths likely to be met with in practice is materially less than is the case with structures available hitherto.

Many other variations are possible within the scope of the following claims. Thus, for example the inner and outer structures 11, 12 can be interconnected at other (e.g. additional) positions around their length and the bag can be secured to the inner structure 11 or to both structures 11, 12 as desired. There can be one or more bags 25 separately or jointly inflatable and within a common sheath or individual sheaths 21.

Furthermore, as an alternative to using an in situ inflatable bag or bags it may be found more convenient to utilise a previously inflated bag or bags selected from a range of bags inflated to a pressure within the range, say, of 30 to 40 mms Hg according to particular requirements.

I claim:

1. A corset comprising a first, inner, band-like structure made from resiliently extensible material and adapted to encircle waists of different girths, a second, outer, band-like structure of inelastic flexible material capable of securement around a wearer's waist in overlying disposition relative to the first band and adaptable to waists of different girths, and an inflatable bag supported by one of said structures in a use position overlying the wearer's abdomen.

2. A corset as claimed in claim 1, further including means for inflating and deflating the bag.

3. A corset as claimed in claim 2, wherein two or more bags are provided, said bags being separately or individually inflatable.

4. A corset as claimed in claim 1, wherein the bag is disposed between the first and second band-like structures.

5. A corset as claimed in claim 4 wherein the first band-like structure is an elongate sheet of elastic textile material.

6. A corset as claimed in claim 1, wherein the first band-like structure includes overlappable end portions provided with complementary areas of hook/pile fasteners cooperable to secure such end portions together in a relative disposition according to the girth of the wearer.

7. A corset as claimed in claim 1, wherein the first band-like structure is adjustable in length by having its ends securable to each other by straps or connectors.

8. A corset as claimed in claim 4, wherein the second band-like structure is an elongate sheet of inelastic textile material.

9. A corset as claimed in claim 1, wherein the second band-like structure is in the form of an abdomen panel laterally connected to one or more straps securable about a wearer's waist.

10. A corset as claimed in claim 9, wherein the second band-like structure comprises two spaced apart straps, each attached to the first band-like structure at the back of the corset and each adjustably engaging the abdomen panel.

11. A corset as claimed in claim 1, wherein the first and second band-like structures are secured to each other, permanently or releasably at the back of the corset.

12. A corset as claimed in claim 1, wherein the first band-like structure includes one or more stiffeners extending transversely of its length.

13. A corset as claimed in claim 9, wherein the abdomen panel is composed of a sheath which encloses the inflatable bag.

14. A corset as claimed in claim 13, wherein the sheath has a rigid plate on the outer side of the inflatable bag.

15. A corset as claimed in claim 1, wherein the inflatable bag has a connected air-flow tube with a non-return valve, a pump bulb being provided for introducing air.

16. A corset comprising first and second open-ended band-like structures arranged in overlying disposition and secured together at a position remote from the ends thereof, fastening means for individually connecting together the opposed ends of the respective bands, and an inflatable bag disposed between the first and second band-like structures and positionable relative to the abdomen of a wearer by such structures, the innermost band-like structure, in the wear condition of the corset, being of a resiliently extensible material, and the outermost such structure being of a relatively inextensible material.

17. A corset as claimed in claim 16, wherein the outermost band-like structure, in the wear condition of the corset, comprises an abdomen panel connected to a plurality of spaced parallel straps, the abdomen panel including a sheath to receive the inflatable bag and a rigid plate disposed within the panel and outwardly of the inflatable bag.

* * * * *